(12) United States Patent
Juntunen et al.

(10) Patent No.: US 8,405,029 B2
(45) Date of Patent: Mar. 26, 2013

(54) PHOTODIODE ARRAY OUTPUT SIGNAL MULTIPLEXING

(75) Inventors: Mikko Juntunen, Kirkkonummi (FI); Iiro Hietanen, Härkäpää (FI)

(73) Assignee: Detection Technology Oy, Micropolis (FI)

( * ) Notice: Subject to any disclaimer, the term of this patent is extended or adjusted under 35 U.S.C. 154(b) by 0 days.

(21) Appl. No.: 12/440,361

(22) PCT Filed: Sep. 7, 2007

(86) PCT No.: PCT/IB2007/003514
§ 371 (c)(1),
(2), (4) Date: Jan. 25, 2010

(87) PCT Pub. No.: WO2008/029284
PCT Pub. Date: Mar. 13, 2008

(65) Prior Publication Data
US 2010/0142782 A1      Jun. 10, 2010

(30) Foreign Application Priority Data
Sep. 7, 2006   (GB) .................................. 0617590.5

(51) Int. Cl.
*H01L 25/00* (2006.01)

(52) U.S. Cl. ...................................... 250/332

(58) Field of Classification Search .................. 250/332, 250/370.01–370.15; 378/98.8
See application file for complete search history.

(56) References Cited

U.S. PATENT DOCUMENTS

| 4,242,706 | A | 12/1980 | McCormack et al. |
| 4,943,491 | A | 7/1990 | Norton et al. |
| 5,304,500 | A | 4/1994 | Timlin et al. |

(Continued)

FOREIGN PATENT DOCUMENTS

| EP | PCT/IB2007/003514 | 3/2008 |
| GB | 2332562 | 6/1999 |

(Continued)

OTHER PUBLICATIONS

Habte et al., "Study of low noise multichannel readout electronics for high sensitivity PET systems based on avalanche photodiode arrays," 2004, IEEE Transactions on Nuclear Science, vol. 51, No. 3, pp. 764-769.*

(Continued)

*Primary Examiner* — Kiho Kim
(74) *Attorney, Agent, or Firm* — Ryan, Mason & Lewis, LLP

(57) ABSTRACT

There is disclosed an imaging system comprising: a first integrated circuit including a photodiode array comprising a plurality of integrating photodiode elements formed in an array of rows and columns, the integrated circuit providing a plurality of output signals corresponding to an output of each photodiode; and a second integrated circuit for receiving as inputs the plurality of output signals from the first integrated circuit and including a plurality of multiplexers corresponding to the number of columns in the array, the outputs signals from a respective column forming inputs to a respective multiplexer, each multiplexer for selectively connecting one of the output signals to a multiplexer output, wherein each multiplexer is selectively switched between the plurality of output signals by a plurality of control lines, the number of control lines corresponding to the number of rows in the array.

11 Claims, 1 Drawing Sheet

U.S. PATENT DOCUMENTS

| | | | |
|---|---|---|---|
| 5,354,980 A | 10/1994 | Rappoport et al. | |
| 5,449,908 A | 9/1995 | Wadsworth et al. | |
| 5,610,389 A | 3/1997 | Asatourian | |
| 5,726,500 A | 3/1998 | Duboz et al. | |
| 5,825,033 A | 10/1998 | Barrett et al. | |
| 6,346,700 B1 | 2/2002 | Cunningham et al. | |
| 6,396,898 B1 | 5/2002 | Saito et al. | |
| 6,510,195 B1 * | 1/2003 | Chappo et al. | 378/19 |
| 2004/0012684 A1 | 1/2004 | Tinnerino | |
| 2004/0100461 A1 | 5/2004 | Fortier | |
| 2006/0038902 A1 | 2/2006 | Boemler | |

FOREIGN PATENT DOCUMENTS

| | | |
|---|---|---|
| GB | 0617590.5 | 1/2008 |
| GB | 0617590.5 | 3/2011 |
| WO | WO95/28006 | 10/1995 |

OTHER PUBLICATIONS

Labanti et al., "ICARUS ASIC: A 16 cahnel phto Diode Read Out System," 1999, IEEE Transactions on Nuclear Science, vol. 46, No. 3, pp. 144-149.*

* cited by examiner

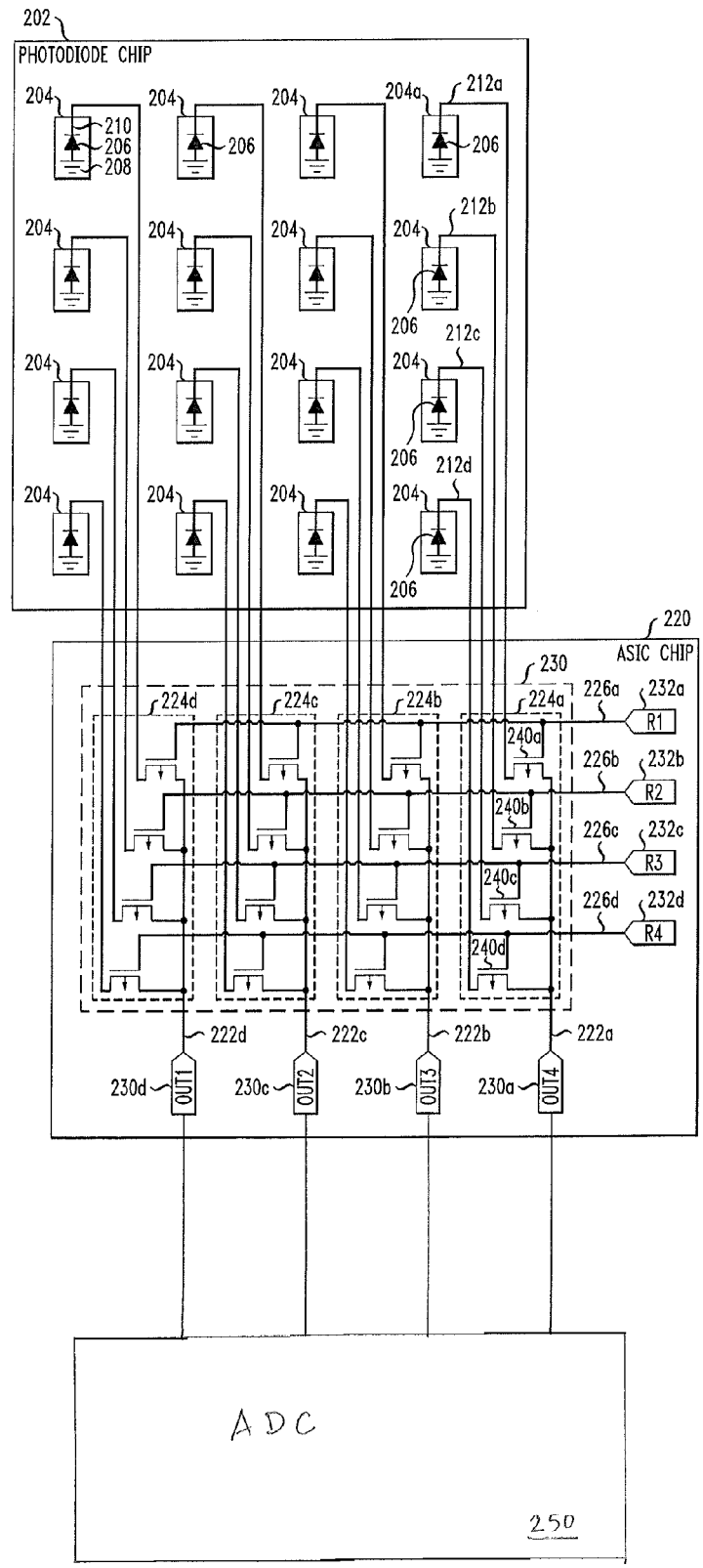

PHOTODIODE ARRAY OUTPUT SIGNAL MULTIPLEXING

The present application claims priority to the international patent application identified as PCT/IB2007/003514 filed on Sep. 7, 2007, which itself claims priority to the UK patent application identified as GB 0617590.5 filed on Sep. 7, 2006, the disclosures of which are both incorporated herein by reference in their entirety.

FIELD OF THE INVENTION

The present invention relates to photodiode arrays for use, for example, in imaging systems and in particular the read-out of signals from such arrays.

BACKGROUND OF THE INVENTION

Photo-detectors are used in imaging systems for medical, security and industrial applications. One particular application of photo-detectors is in computed tomography (CT) systems.

In a typical CT system, an X-ray source with a fan-shaped or cone-shaped X-ray beam and a two-dimensional radiation detector array are assembled on a mechanical support structure, known as a gantry. In use, the gantry is rotated around an object to be imaged in order to collect X-ray attenuation data from a constantly changing angle with respect to the object. The plane of the gantry rotation is known as an imaging plane, and it is typically defined to be the x-y plane of the coordinate system in a CT system. In addition, the gantry (or more typically the object) is moved slowly along the z-axis of the system in order to collect X-ray attenuation data for a required length of the object. By way of background, examples of CT systems can be found in U.S. Pat. Nos. 6,144,718 and 6,173,031.

The radiation detectors of current state of the art CT systems typically consist of a two-dimensional array of rare earth metal based scintillators and a corresponding two-dimensional array of silicon photodiode detectors. The present invention is related to the detectors. In order to present 3-D image data useful for the user of the CT system, complex reconstruction algorithms and software are utilised after or during data collection from the photodiode detectors.

A typical prior art detector consists of an array of rows and columns of individual detector elements. Columns are organised in the z-axis direction. The elements in rows are in the imaging plane, and produce sets of data known as 'slices'. In a medical CT machine, for example, each slice image corresponds to a two-dimensional X-ray image of a thin slice of a human body as seen in the direction of the body axis and the machine z-axis. With current technologies a typical high end detector module (also known as a detector block or detector assembly) consists of 64 rows and 16 or 24 columns of individual detector elements, i.e. 1024 or 1536 elements in total.

In CT imaging systems, the size of the detector in the imaging plane is increased by placing individual detector modules, adjacent to each other to thereby increase the size of the detector in the imaging plane. A complete CT system may typically consist of 35-60 detector modules assembled side-by-side in order to build a complete arc-shaped CT detector.

Typical prior art CT detectors operate in such a way that each photodiode element behaves as a current source whose magnitude is dependent upon the intensity of light impinging upon that particular element. This light signal is integrated outside the photodiode chip by a separate preamplifier. This preamplifier must be permanently connected to the photodiode. There are thus as many preamplifiers in the CT system as there are photodiodes.

A trend in the CT industry is to develop efficient read-out electronics and read-out techniques. There is also a desire to use new technology to lower the cost of less advanced CT systems, thus making better imaging performance available to customers not able to acquire the most expensive systems.

Another trend is to build CT machines with more detector elements in the z-axis direction. A photo-detector with the possibility of expansion in the z-axis direction is known as a 'tileable' detector. An increase in the number of detector elements in the z-axis direction has advantages in various imaging applications. However this trend for tileable detectors further exacerbates other problems, as they potentially lead to top-end CT machines with increasing numbers, potentially without limit, of detector elements in the z-axis direction. There is a general desire to limit the problems of growth, cost and power consumption of detectors in high-end CT systems having an increased number of detector elements.

With typical prior art photodetectors, increasing the number of elements in the z direction is challenging since there must be a path for the signal of every single photodiode to the respective preamplifiers and the data acquisition system of the CT machine. A number of solutions have been provided for providing such connections, which are particularly advantageous as the number of detectors in the z direction increase. Examples of such solutions are back-illuminated photodiodes, and other techniques as disclosed in WO2004/012274 and WO1004/017429 for example. However these techniques do not provide a solution for reducing the complexity of the processing electronics since every photodiode element is still required to have a dedicated preamplifier and associated following stages of electronics.

The trend, toward new read-out electronics and read-out techniques for advanced. CT detectors has overlapping goals with the need for lower costs for less-advanced CT detectors.

U.S. Pat. No. 6,396,898 describes an alternative way for arranging the readout of photodiodes in an array which provides a solution to decrease the number of preamplifiers required in the read-out circuitry of a CT detector. An on-chip multiplexing scheme provides for a number of photodiode elements on one photodiode chip to share a common readout line in order to greatly reduce the number of signal outputs from the photodiode chip, and to correspondingly reduce signal interconnections between the photodiode chip and the preamplifier electronics external to it. Each photodiode serves as a charge integrating capacitor from which the integrated charge will be transferred into a charge sensitive preamplifier in a short readout period. A number of photodiode elements may be read out sequentially, in a time multiplexed manner, by connecting the photodiode elements sharing the same readout line one-by-one to the actual read-out line and the preamplifier connected to it. In practise this is accomplished by manufacturing a switch for each photodiode element and using these switches to perform the multiplexing function. In the simplest case, such switches can be built using individual MOS transistors.

Whilst this solution simplifies the processing circuitry associated with the photodiode array, it leads to further problems. One problem is that the manufacturing process of the photodiode array requires increased complexity, to include the multiplexing circuitry. Another problem is that due to their proximity to the photodiodes, light from the scintillators or radiation can impair the performance of, or deteriorate, the multiplexer switches.

Embodiments of the present invention aim to address one or more of the above problems.

SUMMARY OF THE INVENTION

In accordance with one aspect of the invention there is provided a photo detector module including: a first integrated circuit including an array of photodiodes, an output of each photodiode forming an output signal of the first integrated circuit; and a second integrated circuit for receiving as inputs the output signals of the first integrated circuit, and for selectively connecting the output signals to at least one array output signal.

The array of photodiodes may be integrating photodiodes. A capacitor may be connected in parallel across each photodiode.

The number of array output signal lines may be less than the number of array output signals.

A plurality of the output signals may be grouped, such output signals being for selectively connecting to one array output signal.

There may be provided a plurality of grouped output signals, each for selectively connecting to a respective array output signal.

The second integrated circuit may include a multiplexing means, the multiplexing means including a multiplexer associated with each column of the photodiode array, wherein the output signals of each column are provided as inputs to the respective multiplexer, for multiplexing onto a single array output signal.

The array may comprise a plurality of rows, the multiplexing means adapted to receive a plurality of control signals corresponding to the number of rows and for selecting an output signal from each column for connection to the array output signal.

Each multiplexer may comprise a plurality of switches. The switches may comprise transistors.

The at least one array output signal may form at least one output of the second integrated circuit.

The at least one array output signal may form at least one input to processing circuitry on the second integrated circuit.

Further in accordance with the present invention there is provided an imaging system comprising: a first integrated circuit including a photodiode array comprising a plurality of integrating photodiode elements formed in an array of rows and columns, the integrated circuit providing a plurality of output signals corresponding to an output of each photodiode; and a second integrated circuit for receiving as inputs the plurality of output signals from the first integrated circuit and including a plurality of multiplexers corresponding to the number of columns in the array, the outputs signals from a respective column forming inputs to a respective multiplexer, each multiplexer for selectively connecting one of the output signals to a multiplexer output, wherein each multiplexer is selectively switched between the plurality of output signals by a plurality of control lines, the number of control lines corresponding to the number of rows in the array.

The imaging system may be a CT imaging system.

BRIEF DESCRIPTION OF DRAWINGS

For a better understanding of the present invention, and to show as to how the same may be carried into effect, reference will now be made by way of example to the accompanying drawings in which:

FIG. 1 (depicted simply as the "Figure" in the accompanying drawing) illustrates an output signal multiplexing arrangement in accordance with a preferred embodiment of the invention.

DESCRIPTION OF PREFERRED EMBODIMENTS OF THE INVENTION

The present invention is described hereinafter with reference to a particular set of embodiments. However the invention is not limited to such embodiments.

The invention is particularly described herein with reference to an example of a photo-detector array, comprising a plurality of photodiodes, for a CT medical imaging system.

It should be noted that whilst the invention is illustrated herein by way of reference to various figures, none of these figures are drawn to scale, but rather are drawn to best illustrate various features of the present invention.

Referring to FIG. 1 there is schematically illustrated a photodiode chip 202. The photodiode chip 202 comprises a plurality of photodiodes 204. Reference numerals 204 denote regions of the chip in which single photodiode devices are formed. The photodiodes form an array arranged in rows and columns.

Each photodiode of the photodiode array is preferably an integrating photodiode element as disclosed in U.S. Pat. No. 6,396,898. Each photodiode is manufactured with a higher capacitance than in a typical conventional approach. The provision of the higher capacitance allows the photodiode to integrate the detected signal. The operation of each photodiode to detect and integrate a signal in accordance with preferred embodiments of the invention will be further described below.

Each photodiode is comprised of a pn or np junction forming a pn or np photodiode. As illustrated further in FIG. 1, each formed photodiode 204 functionally forms a diode 206 having a cathode and an anode. Depending on the chosen implementation the output of the photodiode may be provided by the anode or the cathode.

In the example of FIG. 1 the photodiodes are formed of np junctions forming np photodiodes. An anode 208 of each diode 206 is connected to ground, with a cathode 210 of each diode 206 forming an output of the photodiode. The output of each photodiode is connected to an output signal line 212. The number of output signal lines 212 corresponds to the number of photodiodes in the array. In the simplified example of FIG. 1 there are sixteen photodiodes and therefore sixteen output signal lines 212.

In accordance with the invention the output signal line of each photodiode is connected off-chip. The output signal lines are connected to form inputs to a further chip 220. The further chip 220 is preferably an ASIC (application specific integrated circuit) chip.

The ASIC chip 220 provides signal multiplexing of the output signal lines 212 from a selected group of photodiode outputs to a single common readout signal line. In the exemplary arrangement illustrated the output signal lines from all photodiodes in one column of the two-dimensional array of photodiodes on one photodiode chip are connected via a multiplexer to a single common readout signal line.

Thus the output signal lines 212 form inputs to the ASIC chip 220, which are provided as inputs to a multiplexer 230 formed in the ASIC chip 220. The multiplexer additionally receives read control inputs on read control signal lines 226, and generates a set of outputs on common readout signal lines 222.

The multiplexer 230 effectively comprises a set of sub-multiplexers 224. Each sub-multiplexer 224 is associated with one selected group of photodiode outputs, such that the sub-multiplexers 224 multiplex the output signal lines 212 from a selected group of photodiode outputs to a single common readout signal line 222.

In the exemplary arrangement of FIG. 1, the number of sub-multiplexers 224 corresponds to the number of columns in the photodiode array. All photodiodes in the same column have their output, signal lines grouped together and connected as inputs to one of the sub-multiplexers 224.

The sub-multiplexers 224 are controlled by the set of readout control signals on lines 226. The number of readout control signals corresponds to the number of grouped output lines, which in turn corresponds to the number of photodiodes in a column of the photodiode array. The readout control signals control the sub-multiplexers 224 to select only one of the output signal lines 212 to be connected to a readout signal line 222 at any one time.

In the exemplary arrangement the readout control lines control the sub-multiplexers 224 such that the outputs from a common row of each column of the photodiode array are provided as the readout signals at any given time.

The multiplexers are preferably implemented as a set of switches, which switches are controlled such that only one is closed at any one time to connect an output signal line 212 to a common readout signal line 222. Each switch receives as an input one of the output signal lines 212, and is switchably connected to a common readout signal line 222. The readout control signals on lines 226 determine which switch is connected at any instant.

Each photodiode 204 on the photodiode chip 202 (for example photodiode 204a) is thus associated with a switch (for example switch 240a) on the ASIC chip 220. The switch 240a connects and disconnects the photodiode 204a from the common readout signal line 222a, which common readout signal line is preferably common to all photodiodes in the same column.

In practice the readout operation of the photodiode array can be summarised as follows.

During an initial readout sequence one photodiode of a column is connected to the associated common readout signal line and hence to the associated column preamplifier (not shown in FIG. 1). This photodiode, which behaves like a capacitor, is charged to a voltage, for example +1.0V.

After the readout reset sequence, the switch associated with that photodiode is disconnected from the readout line and is placed in a non-conductive state. The photodiode is then floating and is disconnected for a certain period of time. This time period is the photodiode integration time. The photodiode behaves like a capacitor pre-charged to an initial voltage of +1.0V and with a current source in parallel with the capacitor. As a result the voltage of the photodiode capacitor starts dropping toward 0V. The rate at which the voltage drops depends on the light intensity from the scintillators and the following current source intensity of the photodiode.

In a following readout period, the photodiode is again connected to the column preamplifier. The preamplifier recharges the photodiode capacitor back to +1.0V. Whilst the preamplifier feeds the recharging current to the photodiode, the preamplifier also measures the amount of charge required to return the voltage back to +1.0V. Hence, the readout signal from the photodiode is the drop in the preset voltage of each photodiode element during an integration period. That drop is measured by the preamplifier when the photodiode connects to it after the integration period.

With this technique, one column preamplifier can be used to read the output signals from a plurality of photodiodes in one column, by successively reading out signals from each row of the column in a cyclical manner.

The switches are preferably implemented as transistors, with the control node of the transistors receiving the readout control signal on line 226. The number of switches or transistors in each multiplexer corresponds to the number of rows in the photodiode array.

Thus, for example, the sub-multiplexer 224a comprises four transistors 240a to 240d. A first transistor 240a has a control node connected to the readout control signal on line 226a, and a conductive path connected between the output signal line 212a and the common readout signal line 222a. A second transistor 240b has a control node connected to the readout control signal on line 226b, and a conductive path connected between the output signal line 212b and the common readout signal line 222a. A third transistor 240c has a control node connected to the readout control signal on line 226c, and a conductive path connected between the output signal line 212c and the common readout signal line 222a. A fourth transistor 240d has a control node connected to the readout control signal on line 226d, and a conductive path connected between the output signal line 212d and the common readout signal line 222a.

In FIG. 1 an exemplary multiplexing arrangement is shown, where photodiode elements in one row of the photodiode chip share a common control line for controlling the multiplexing signal switches, and all photodiodes elements in one column of the photodiode chip share a common readout signal line after the multiplexing signal switches. However, the configuration of control signals and readout lines are not limited to this arrangement and one skilled in the art will appreciate that alternative readout arrangements from that illustrated may be used.

Whilst the preferred embodiment is disclosed as being a single common readout signal line which is common to one column of the photodiode array, a single readout signal line may be provided to connect to more than one column, if the requirements for readout speed can be met.

The general principle of the multiplexing is that the number of output signal lines presented for signal processing from the photodiode array is reduced relative to the number of signal output lines provided by the photodiode array. Any technique which achieves this may be used for multiplexing the output signals from the photodiodes to a reduced set of readout signal lines. The invention thus provides a solution to reduce the number of interconnects from the photodiode array to the processing circuitry, and consequently the amount of processing circuitry required. Whilst the number of interconnects between the photodiode chip and ASIC chip are equal to the number of photodiodes in the photodiode array, this is outweighed by the advantages achieved in providing the photodiode array on a separate chip to the multiplexing circuitry.

The invention provides a technique for multiplexing the output signals from an array of photodiodes, preferably utilising the integration of signals in the photodiodes, without increasing the complexity of the photodiode chip by providing a separate chip for the multiplexing functionality and accepting no reduction in the number of interconnects between the photodiode chip and the separate multiplexing chip.

In the preferred embodiment, as described above, the photodiodes are formed in accordance with the techniques disclosed in U.S. Pat. No. 6,396,898. However any photodiode structure which allows the photodiodes to be disconnected from a readout signal line during operation may be used. This may not be limited to arrangements in which the photodiodes float whilst disconnected.

In accordance with the invention, the photodiode chip consists only of the photodiodes forming the photodiode array, together with any associated signal lines. The design and manufacturing process for such a photodiode chip is thus advantageously simplified compared to prior art arrangements, in, which the multiplexing circuitry is additionally provided on the photodiode chip. The simplification also advantageously results in the manufacturing cost of the chip being lowered. A switch is provided for each photodiode element, but the switch is provided on a chip or integrated circuit separate and distinct from the chip on which the photodiode array is provided.

The readout control signals on line 226 are illustrated in FIG. 1 as being provided on input pads 232 of the ASIC chip, on the assumption they are generated off-chip. A digital control circuit, such as a shift register, may provide the readout control signals, and this circuit may be provided on the ASIC chip 220 or off-chip. The control circuit, such as the shift register, may merely cycle through an appropriate count corresponding to the number of rows in order to control the read out of signals from the photodiode array.

In FIG. 1 the ASIC chip is shown connecting the common readout signal lines 224 to output pads 230 of the ASIC chip. However the ASIC chip 220 may perform additional functions after the output signals are multiplexed onto the readout lines. As mentioned hereinabove each common readout signal line is preferably connected to a preamplifier for first level signal processing. Such preamplifiers may also be provided on the ASIC chip 220. The output of the integrating preamplifiers may further connect to additional signal processing stages. Still further the signals of the shared signal lines could be processed all the way to digital signals using analog-to-digital converters (ADC) on the ASIC chip 220 or on an another commercial or custom designed ASIC circuit in the immediate vicinity of the ASIC chip 220 shown in FIG. 1. Block 250 represents an additional integrated circuit including analog-to-digital converters, which additional integrated circuit receives input signals from the output pads 230 of the ASIC chip 220.

Embodiments of the invention thus present a multiplexing scheme, where each photodiode shares a common readout signal line with other photodiodes on the same photodiode chip, but the switches enabling such multiplexed operation are not provided on the photodiode chip itself. Instead, the switches are placed on a separate chip, such as an ASIC chip manufactured utilizing commercially available CMOS (Complementary Metal-Oxide-Semiconductor) technology.

The photodiodes manufactured on the photodiode chip accumulate and integrate the signal charge in accordance with the techniques described above. However, since in accordance with embodiments of the invention the switches required for the multiplexed operation are external to the photodiode chip, the photodiode chip construction and manufacturing process is advantageously simplified and the cost of the manufacturing process is lowered. In addition the photodiode chip may advantageously be manufactured on a less expensive starting wafer material.

The provision of the multiplexing switches of the photodiodes on a separate chip enables the use of high quality properties of MOS transistor based switches. By provision on a separate chip to the photodiodes these switches can advantageously be protected from light emitted by the scintillators and from radiation. In such an arrangement according to embodiments of the invention, advantageously the multiplexer switches do not exhibit leakage due to exposure to stray light from scintillators, and the properties of the switches do not deteriorate due to radiation exposure to the same extent as switches which are placed near the active photodiode elements. The readout signal lines and control circuitry for controlling the multiplexer are similarly protected from stray light or radiation.

Embodiments of the invention results in an interconnection density between the photodiode chip and the ASIC chip which is similar to that found in conventional CT semiconductor detectors. Interconnection density is higher than in the multiplexing approach of U.S. Pat. No. 6,396,898. However this is not a limiting factor especially in the design and manufacturing of less advanced, low cost CT systems, and particularly when the various technical advantages achieved by the separation are understood.

The photodiodes manufactured on the photodiode chip are designed to exhibit a capacitance allowing integration of light generated current signal into each photodiode element while the diode is disconnected from any electronics outside the photodiode chip. The capacitance of each photodiode element may include the capacitance inherent to the depletion region of the photodiode, but each photodiode element may also have an additional capacitor processed on the photodiode chip to increase the capacitance and charge storage capability of each element on the photodiode chip. Schematically, such a capacitor may be connected in parallel across a photodiode element. This increases the total capacitance of a photodiode element.

The multiplexing techniques and arrangements of embodiments of the invention as described herein further offer particular advantages in so-called 'tileable' imaging systems. In tileable imaging systems the number of output signals to be processed simultaneously is larger than in conventional imaging systems, since photodiode arrays may be placed side-by-side in two dimensions in an unconstrained manner, increasing the number of output signals generated. The invention allows the amount of processing circuitry required to be reduced by multiplexing the output signals in a time-dependent manner.

A photo-detector array constructed in accordance with the principles of a preferred embodiment of the present invention may advantageously be used in a CT imaging system. Other useful and advantageous applications will be apparent to one skilled in the art.

It should be understood that the invention is more generally applicable than the examples given herein. One skilled in the art will understand the broader applicability of the present invention. The scope of the invention is defined by the appended claims.

The invention claimed is:

1. A photo detector module including:
   a first integrated circuit including an array of photodiodes arranged in rows and columns, an output of each photodiode forming an output signal of the first integrated circuit; and
   a second integrated circuit for receiving as inputs the output signal of each photodiode of the first integrated circuit, the second integrated circuit including a multiplexer associated with each column of the photodiode array, wherein the output signal of each photodiode of each column of the photodiode array are grouped to provide inputs to the respective multiplexer, for multiplexing one of the plurality of output signals of the column onto a single array output signal for the column, the number of output signals of the second integrated circuit corresponding to the number of columns in the photodiode array.

2. A detector according to claim 1 wherein the array of photodiodes are integrating photodiodes.

3. A detector according to claim 1 further including a capacitor connected in parallel across each photodiode.

4. A detector according to claim 1 wherein the multiplexer is adapted to receive a plurality of control signals corresponding to the number of rows and for selecting an output signal from each column for connection to the array output signal.

5. A detector according to claim 1 wherein each multiplexer comprises a plurality of switches.

6. A detector according to claim 5 wherein the switches comprise transistors.

7. A detector according to claim 1 wherein the at least one array output signal forms at least one output of the second integrated circuit.

8. A detector according to claim 1 wherein the at least one array output signal forms at least one input to processing circuitry on the second integrated circuit.

9. An imaging system comprising:
a first integrated circuit including a photodiode array comprising a plurality of integrating photodiode elements formed in an array of rows and columns, the integrated circuit providing a plurality of output signals corresponding to an output of each photodiode;
a second integrated circuit for receiving as inputs the plurality of output signals from the first integrated circuit and including a plurality of multiplexers corresponding to the number of columns in the array, the output signals from each respective column forming inputs to a respective multiplexer, each multiplexer for selectively connecting one of the output signals to a multiplexer output, wherein each multiplexer is selectively switched between the plurality of output signals by a plurality of control lines, the number of control lines corresponding to the number of rows in the array, the multiplexer outputs forming output signals of the second integrated circuit, the number of output signals corresponding to the number of columns in the photodiode array; and
a third integrated circuit for receiving as inputs the output signals of the second integrated circuit and for performing analog-to-digital conversion of such signals, the number of analog-to-digital conversion circuits on the third integrated circuit corresponding to the number of columns in the photodiode array.

10. A CT imaging system comprising:
a first integrated circuit including a photodiode array comprising a plurality of integrating photodiode elements formed in an array of rows and columns, the integrated circuit providing a plurality of output signals corresponding to an output of each photodiode;
a second integrated circuit for receiving as inputs the plurality of output signals from the first integrated circuit and including a plurality of multiplexers corresponding to the number of columns in the array, the output signals from each respective column forming inputs to a respective multiplexer, each multiplexer for selectively connecting one of the output signals to a multiplexer output, wherein each multiplexer is selectively switched between the plurality of output signals by a plurality of control lines, the number of control lines corresponding to the number of rows in the array, the multiplexer outputs forming output signals of the second integrated circuit, the number of output signals corresponding to the number of columns in the photodiode array; and
a third integrated circuit for receiving as inputs the output signals of the second integrated circuit and for performing analog-to-digital conversion of such signals, the number of analog-to-digital conversion circuits on the third integrated circuit corresponding to the number of columns in the photodiode array.

11. A CT system comprising a photo detector module comprising:
a first integrated circuit including an array of photodiodes arranged in rows and columns, an output of each photodiode forming an output signal of the first integrated circuit; and
a second integrated circuit for receiving as inputs the output signal of each photodiode of the first integrated circuit, the second integrated circuit including a multiplexer associated with each column of the photodiode array, wherein the output signal of each photodiode of each column of the photodiode array are grouped to provide inputs to the respective multiplexer, for multiplexing one of the plurality of output signals of the column onto a single array output signal for the column, the number of output signals of the second integrated circuit corresponding to the number of columns in the photodiode array.

* * * * *